United States Patent [19]

Hasegawa et al.

[11] Patent Number: 5,127,834
[45] Date of Patent: Jul. 7, 1992

[54] ARTIFICIAL TEETH AND METHOD FOR MAKING THEM

[75] Inventors: Akira Hasegawa, Inuyama; Yuji Nakamura; Ikuo Ikeda, both of Kasugai, all of Japan

[73] Assignee: G-C Toshi Kogyo Corporation, Kasugai, Japan

[21] Appl. No.: 451,994

[22] Filed: Dec. 18, 1989

[30] Foreign Application Priority Data

Dec. 28, 1988 [JP] Japan ................................. 63-329167

[51] Int. Cl.$^5$ ................................................ A61C 9/00
[52] U.S. Cl. .............................. 433/202.1; 433/203.1; 433/212.1; 433/201.1
[58] Field of Search ................ 433/202.1, 203.1, 212.1, 433/229, 201.1

[56] References Cited

U.S. PATENT DOCUMENTS 4,744,827 5/1988 Winkel et al. .
4,752,338 6/1988 Reiners .

Primary Examiner—V. Millin
Attorney, Agent, or Firm—Oblon, Spivak, McClelland, Maier & Neustadt

[57] ABSTRACT

An artificial tooth comprised of an enamel segment, a composite material of a resin matrix composed mainly of a polymerizable compound with a urethane bond and at least two ethylenically unsaturated double bonds, optionally with a polymerizable compound with at least two ethylenically unsaturated double bonds; and a dentinal segment, a composite material of polymethylmethacrylate, methylmethacrylate, one or more of a polymerizable compound with a urethane bond and at least two ethylenically unsaturated double bonds, one or more of a polymerizable compound with at least two ethylenically unsaturated double bonds, one or more of a polymerizable compound with a phenyl group and at least two ethylenically unsaturated double bonds, and one or more of a polymerizable compound with a urethane bond, a phenyl group, and at least two ethylenically unsaturated double bonds. For the preparation of the artificial tooth, the dentinal segment is first incompletely polymerized without the enamel segment, and the enamel segment is then completely polymerized simultaneously with complete polymerization of the dentinal segment.

4 Claims, No Drawings

ARTIFICIAL TEETH AND METHOD FOR MAKING THEM

BACKGROUND OF THE INVENTION

1. Field of the Invention

The present invention relates to a material for resin teeth usable as foreteeth and molars, which is much more improved in terms of mechanical properties and serves to prevent a color change and coloration of the so-called hard resin teeth heretofore available and to improve the adhesion between the enamel and dentinal segments thereof, and a method for making such material for the resin teeth.

2. Prior Art

Both enamel and dentinal segments of conventional resin teeth are composed primarily of polymethylmethacrylate. The components of the resin teeth which are composed primarily of polymethylmethacrylate before they are formed into products are broken down into powdery and liquid components.

The constituents of the powdery component are granular polymethyl methacrylate, polymerization initiator, colorant and so on, while those of the liquid component are methyl methacrylate, polymerizable compound containing at least two ethylenically unsaturated double bonds, and the like. Two such components are mixed together, thereby swelling the granular polymethyl methacrylate with the methyl methacrylate into pasty state, and the thus formed paste is filled under pressure in a counter-die of a denture mold for thermal polymerization. The thus obtained resin teeth are formed of a material stable with respect to some heat or an organic solvent, since it turns to a heat-curing resin crosslinked with the polymerizable compound containing at least two ethylenically unsaturated double bonds. However, a certain limitation is placed on the mechanical properties of such resin teeth, since they are primarily composed of polymethyl methacrylate. The so-called hard resin teeth currently used in incorporated technically with about 20 to 30% of an inorganic filler with the application of an ultra-fine granule type of composite resin material, thereby improving the mechanical properties of their enamel segments. In most cases, the matrix resins used are a polyfunctional methacrylate with no urethane bond but with a phenyl group and containing at least two ethylenically unsaturated double bonds such as, for example, bisphenol A diglycidyl methacrylate and a polyfunctional methacrylate with both an urethane bond and a phenyl group and containing at least two ethylenically unsaturated double bonds such as, for instance, dimethacryloxyethyl-1,2-dimethylphenyl dicarbamate.

In conventional methods for making resin teeth and the so-called hard resin teeth, incomplete polymerization is followed by complete polymerization to prevent air bubbles from occurring in the interiors of the enamel and dentinal segments due to the heat of polymerization generated at the time of polymerization, thereby ensuring sufficient adhesion of the enamel segments to the dentinal segments. More specifically, the lowest temperature and shortest time required for initial pre-polymerization of the methylmethacrylate or polymerizable compound containing at least two ethylenically unsaturated double bonds are first selected. Then, one of the enamel and dentinal segments is subjected to initial pre-polymerization, viz., incomplete polymerization at a temperature of 60° to 70° C. for 15 to 30 minutes. Subsequently, the one of the enamel or dentinal segments is laminated on the other enamel or dentinal segment, followed by incomplete polymerization again at a temperature of 60° to 70° C. for 15 to 30 minutes to bond both segments together. Finally, complete polymerization is carried out at 90° to 100° C. for 15 to 60 minutes.

The materials of resin teeth and so-called hard resin teeth so far used and the methods for making them involve the following problems.

(1) Essentially, the conventional resin teeth composed primarily of polymethyl methacrylate have a surface Knoop hardness of 15 to 20, this is much lower than 300 and 65 for the enamel and dentin of natural teeth, 463 for porcelain teeth, 90 for amalgam, 70 for silicate cement and 35-50 for composite resin. Thus, not only the enamel but also the dentinal segments may wear away, suffer damage and deform due to attrition and strong chewing during mastication or repeated contact with a toothbrush.

(2) The conventional resin teeth composed mainly of polymethylmethacrylate are so stable at a temperature lower than about 80° to 100° C. that they are very unlikely to melt, since they are crosslinked with the polymerizable compound having at least two ethylenically unsaturated double bonds. However, it is likely that a considerably elevated temperature exceeding 160°-200° C., that is the melting point of polymethyl methacrylate, may be instantaneously reached at the time when milling-in is carried out using a carborundum point or a stamp bar with a dental engine for the purpose of occulusal equilibration. Molten resin teeth deposit on such polishing members, there is an extreme reduction in the efficiency of polishing.

(3) In the process of making dentures, a wax model for dentures is invested with gypsum in a dental flask and is then cast to bond resin teeth to a plate resin by thermal polymerization. In this case, since the resin teeth have a coefficient of thermal expansion of as high as 80 to 100 mm/mm/°C., they are brought in firm contact with the gypsum which shows little or no thermal expansion at the temperature at which the plate resin is polymerized. Thus, the rough surface of gypsum is impressed as such onto the resin teeth which, as a result, lose glaze.

(4) Some of the conventional so-called hard resin teeth are formed of a composite material in which a resin matrix composed mainly of a polyfunctional methacrylate with both an urethane bond and a phenyl group and containing at least two ethylenically unsaturated double bonds such as, for instance, dimethacryloxyethyl-1,2-dimethylphenyl dicarbamate, is combined with an inorganic filler in ultra-finely divided form. Such a composite material suffers color change and coloration in the oral cavity within a short period of time due to natural or synthetic food colors, and is often clinically detected as deposits. Thus, clinical results with such teeth are found unfavorable.

(5) Referring to the so-called hard resin teeth prepared with a composite material in which a resin matrix composed mainly of a polyfunctional methacrylate with no urethane bond but with a phenyl group and containing at least two ethylenically unsaturated double bonds such as, for instance, bisphenol A digylcidyl methacrylate or an unsaturated polyester, is combined with an ultra-finely divided inorganic filler, they are generally very short of transparency which is an important factor for artificial teeth. Hence, the teeth assume clouding upon wetted with saliva or water owing to their refractive indices, since their enamel segments are of no depth, and are so clinically and aesthetically not desirable. Inferior transparency also makes it impossible to produce colorful tones of variety.

(6) The enamel segments of the conventional so-called hard resin teeth are formed of a composite material in which a resin matrix composed mainly of a polyfunctional methacrylate with both an urethane bond and a phenyl group or with no urethane bond but with a phenyl group and containing at least two ethylenically unsaturated double bonds is combined with an ultrafinely divided inorganic filler, and so show very inferior adhesion of the polymethyl methacrylate onto the dentinal segments. For that reason, both the segments are bonded together with no incorporation of an inorganic filler into the dentinal segments, i.e., at the cost of the mechanical properties of the dentinal segments. Therefore, if the enamel segments are polished off to the dentinal segments when milling-in or occlusal equilibration is clinically carried out, then any improvement in physical properties such as wear resistance is not attained, since their unhardened portions are exposed to view.

(7) In conventional methods for making the conventional resin teeth and so-called hard resin teeth, incomplete polymerization is followed by complete polymerization to prevent any air bubbles from occurring in the interiors of the enamel and dentinal segments due to the heat of polymerization generated at the time of polymerization, thereby allowing both segments to be sufficiently bonded together. The making time required is a total of 2 hours, say, 30 minutes for the incomplete polymerization of one of the enamel and dentinal segments + 30 minutes for the incomplete polymerization of the other + 60 minutes for the complete polymerization of both segments.

SUMMARY OF THE INVENTION

As a result of extensive and intensive studies made so as to solve the above problems, it has been found that they can all be solved by using for enamel and dentinal segments the materials having such compositions as mentioned below and making artificial teeth by the following method. For experessional convenience, the compounds involved are defined as follows.

Compound A: a polymerizable compound with an urethane bond but with no phenyl group and containing at least two ethylenically unsaturated double bonds.

Compound B: polymerizable compound containing neither an urethane bond nor a phenyl group but containing at least two ethylenically unsaturated double bonds.

Compound C: a polymerizable compound with no urethane bond but with a pheny group and containing at least two ethylenically unsaturated double bonds.

Compound D: a polymerizable compound with both an urethane bond and a phenyl group and containing at least two ethylenically unsaturated double bonds.

ENAMEL SEGMENT

A composite material comprising (i) a resin matrix composed mainly of one or two or more compounds A with or without one or two or more compounds B and (ii) a filler added to said resin matrix and comprising one or two or more inorganic filler and/or one or two or more organic/inorganic composite filler (hereafter called a filler) and further including (iii) a polymerization initiator catalyst and (iv) a colorant.

DENTINAL SEGMENT

A material comprising (i) polymethylmethacrylate, (ii) methylmethacrylate and (iii) a component cross-linked with one or two or more compounds selected from the group consisting of one or two or more compounds A; one or two or more compounds B; one or two or more compounds C; and one or two or more compounds D and optionally including (iv) a filler, (v) a polymerization initiator catalyst and (vi) a colorant.

MAKING METHOD

A method in which the dentinal segment is first subjected to incomplete polymerization and, just after the enamel segment is laminated thereon, both the segments are finally subjected to complete polymerization. Especially when the compound(s) A has a high viscosity in the preparation of the enamel segment, the preparation of an artificial tooth is very expedited by using the compound(s) B as a viscosity regulator.

The making method will now be explained specifically.

(1) The enamel segment according to the present invention is formed of a composite material in which the above resin matrix is combined with the filler, and so has a surface Knoop hardness of about 45, the figure being higher by about 2-3 times than that of a conventional resin tooth composed mainly of polymethylmethacrylate, methylmethacrylate and a polymerizable compound containing at least two ethylenically unsaturated double bonds. Thus, the enamel segment is very unlikely to wear away, suffer damage or deform due to attrition or strong chewing at the time of mastication and repeated contact with a toothbrush.

(2) The enamel and dentinal segments according to the present invention are formed of a composite material with the filler. The melting point of such a composition is then determined by the proportional relation of the melting point and volume fraction of the resin matrix to the melting point and volume fraction of the filler. Therefore, when silicon dioxide having a melting point of as high as one thousand and hundreds centigrades is used, the melting point of a composite material with it is a few times to ten-and-several times higher than that of a conventional resin tooth composed mainly of polymethylmethacrylate, methylmethacrylate and a polymerizable compound containing at least two ethylenically unsaturated double bonds, even though its volume fraction is slight. Hence, dental operations are very expedited when milling-in is carried out for the purpose of occulusal equilibration, using a carborundum point or a stamp bar with a dental engine, since it is unlikely that the artificial tooth according to the present invention may be deposited onto such polishing members with the resulting drop in polishing efficiency.

(3) Where a denture is prepared with the use of a dental flask, the artificial tooth according to the present invention shows a coefficient of thermal expansion of about 30 to 50 mm/mm/°C., the figure being half or below the coefficient of thermal expansion of a conventional resin tooth. Hence, it is unlikely that the tooth may be brought into firm contact with gypsum by thermal expansion at a temperature ranging from room temperature up to about 100° C. In case the artificial tooth according to the present invention is brought in tight contact with gypsum, it is then unlikely that the rough surface of gypsum may be impressed thereon due to its increased surface hardness. Thus, the artificial tooth according to the present invention cannot be rid of surface glaze, unlike a conventional resin tooth, since it remains smooth on its surface.

(4) Essentially, the artificial tooth according to the present invention contains as the material for its enamel segment the compound A with an urethane bond but with no phenyl group, and is thus more unlikely to suffer color change and coloration in the oral cavity due to natural or synthetic food colors, as compared with the conventional so-called hard resin tooth making use of the compound D containing both an urethane bond and a phenyl group. Nor are any deposits detected clinically whatsoever.

(5) Essentially containing as the enamel segment the compound A with an urethane bond but with no phenyl group, the artificial tooth according to the present invention suffers little or no drop in transparency, even when it is used as a resin matrix and formed into a composite material. In particular, it is so well-compatible with a filler based on silicon dioxide in terms of the index of refraction that its total transmittance can be 65-70%, the index of refraction being much more favorable than that obtained with the compound C containing no urethane bond but having a phenyl group, registering 20-40%. Satisfactory transparency makes it possible to give every color tone to an artificial tooth and to impart a deep color tone to the enamel segment. Even upon wetted with saliva or water, the present artificial tooth is not clouded at all, unlike the conventional so-called hard resin tooth, thus posing no aesthetic problem even when used for clinical purposes.

(6) A problem with the conventional so-called hard resin tooth is that, because of the enamel segment being formed of a phenyl group-containing compound, the adhesion of the enamel segment to the dentinal segment is so poor that the enamel segment may often be peeled from the dentinal segment. According to the present invention, however, it is possible to develop an artificial tooth showing improved enamel-to-dentin adhesion even when a filler is added to the dentinal segment, because the enamel segment is essentially designed to contain the phenyl group-free compound excelling in adhesion to the dentinal segment. Accordingly, improvements in physical properties such as wear resistance are ensured even when the enamel segment is polished off to the depth of dentinal segment following clinical milling-in or occlusal equilibration, because the dentinal segment is hardened by such a filler.

(7) Used for the artificial tooth according to the present invention are one or two or more compounds A with an urethane bond but with no phenyl group with or without one or two or more compounds B with neither an urethane bond nor a phenyl group. Thus, if only the dentinal segment is first incompletely polymerized at a temperature of 60°-70° C. for about 15-30 minutes, the enamel and dentinal segments can then be sufficiently bonded together with no generation of air bubbles in the enamel segment. Later, overlapping portions of both segments can be completely polymerized simultaneously at 90°-120° C. for about 10-30 minutes. This method takes 25-60 minutes for one cycle of denture making to be completed, the figure being about one-third or one-fourth of the length of a conventional cycle.

Included in the compound A to be used for the enamel segment are 7,7,9-trimethyl-4,13-dioxo-3,14-dioxo-5,12-diazahexa-decane-1,6-diol-dimethacrylate, bis(methacryloxyethyl)hydroxyethyl isocyanurate, tris(methacryloxyethyl)isocyanurate and caprolacton-modified tris(methacryloxyethyl)isocyanurate. Also preferable are substances having the following structural formulae or their acrylates:

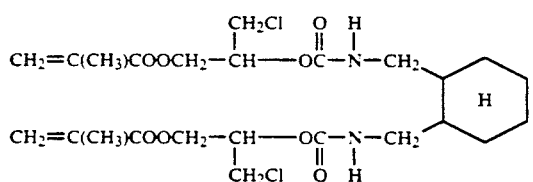

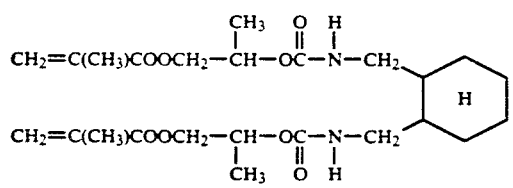

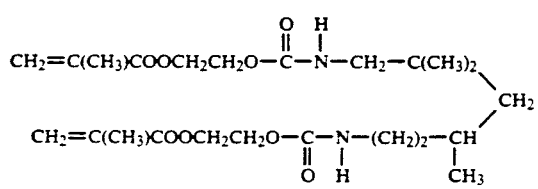

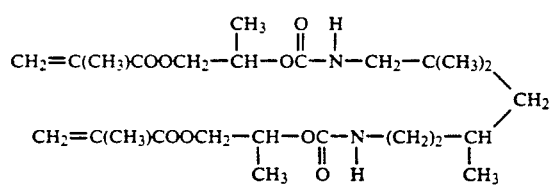

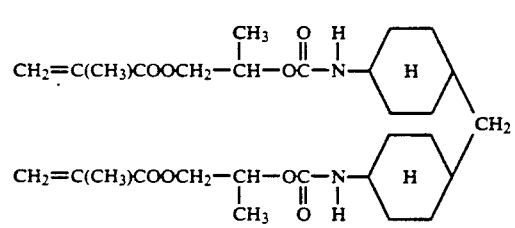

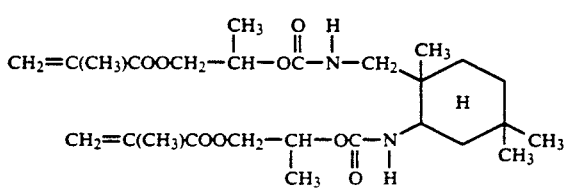

-continued
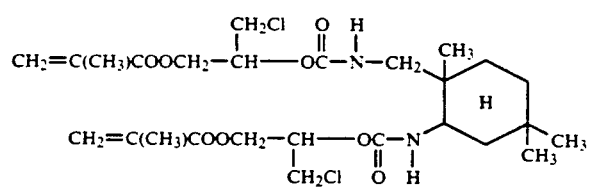
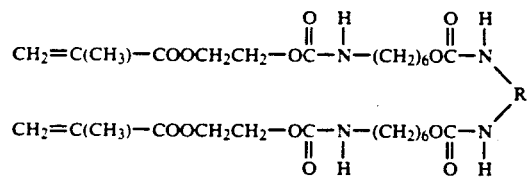
(R is an alkyl group)
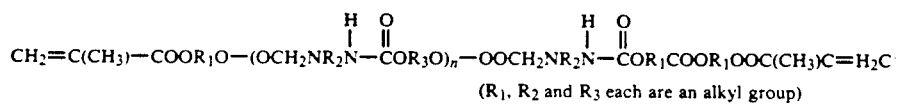
($R_1$, $R_2$ and $R_3$ each are an alkyl group)
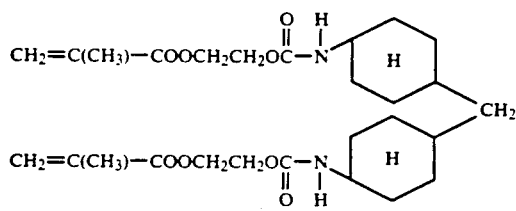
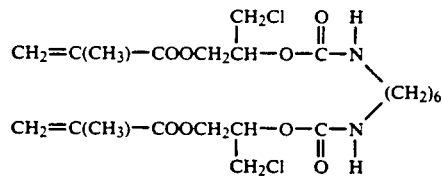
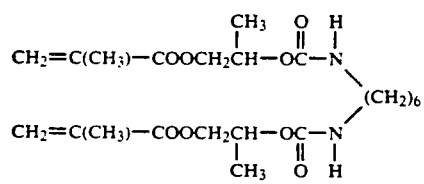
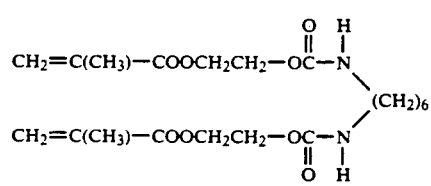
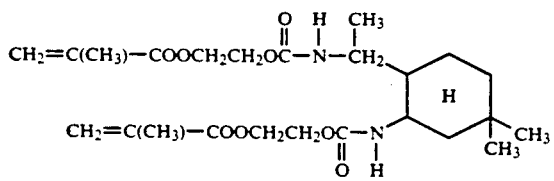
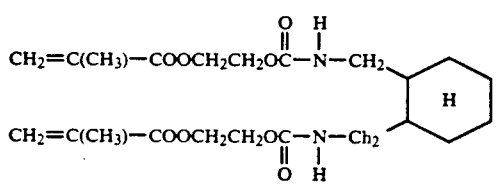
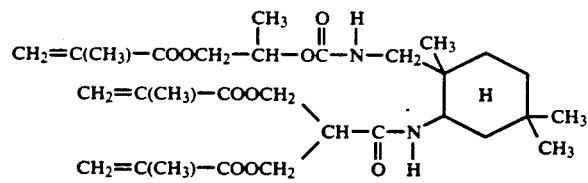
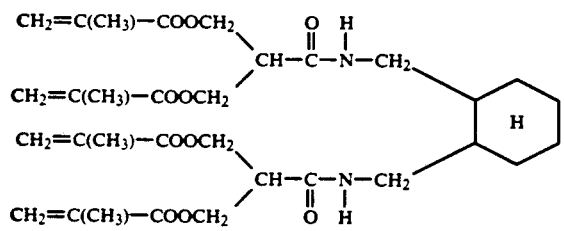
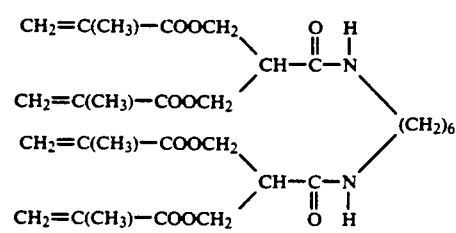

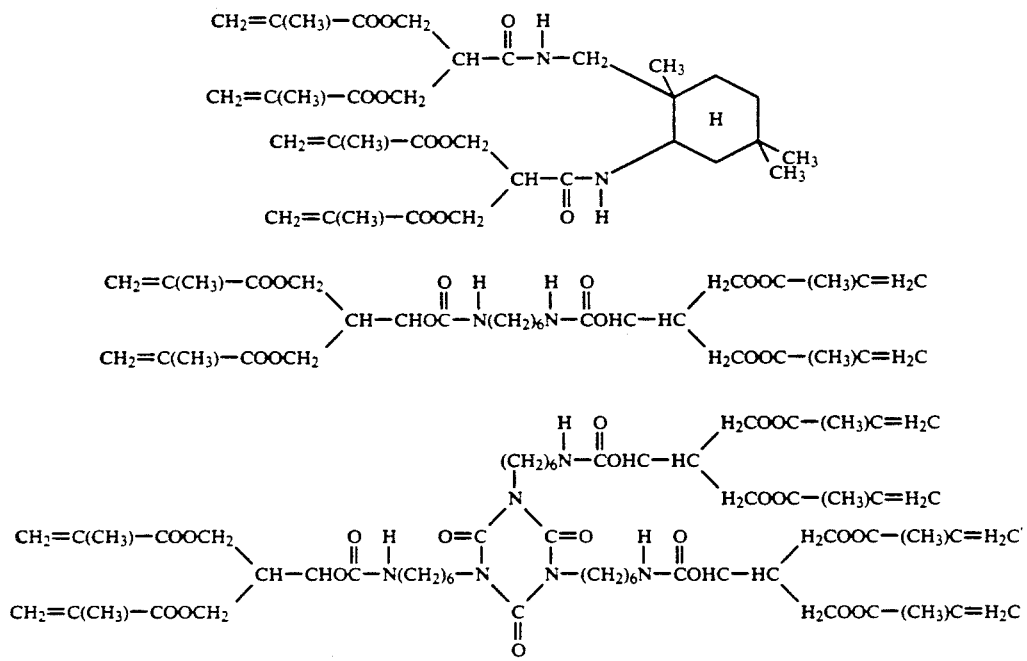

These substances may be used alone or in admixture, preferably with optional pre-addition of polymerization initiator catalysts such as an organic peroxide, e.g., benzoyl peroxide or an azo compound, e.g., azobisisobutylonitrile.

When the compound A has a high viscosity, the compound B is similarly used for the enamel segment as a viscosity regulator. Such a polymerizable compound includes ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol trimethacrylate, trimethylolmethane trimethacrylate, and pentaerythritol tetramethacrylate as well as acrylates thereof. These may be used alone or in admixture, preferably with optional pre-addition of polymerization initiator catalysts such as an organic peroxide, e.g., benzoyl peroxide and an azo compound, e.g., azobisisobutylonitrile.

Both the compound A and the compound B used for the dentinal segment are the same as those used for the enamel segment. In addition, the compound C may include 2,2-bis(methacryloxyphenyl)propane, 2,2-[4-(2-hydroxy-3-methacryloxyethoxyphenyl)]propane, 2,2-bis(4-methacryloxyethoxyphenyl)propane, 2,2-bis(4-methacryloxydiethoxypheny)propane, 2,2-bis(4-methacryloxypropoxyphenyl)propane as well as acrylates thereof.

These may be used alone or in admixture, preferably with optional pre-addition of polymerization initiator catalysts such as an organic peroxide, e.g., benzoyl peroxide and an azo compound, e.g., azobisisobutylonitrile.

The compound D similarly used for the dentinal segment may include:

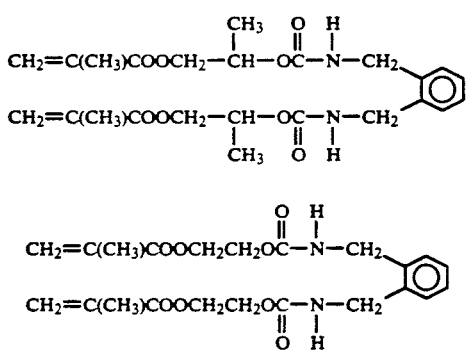
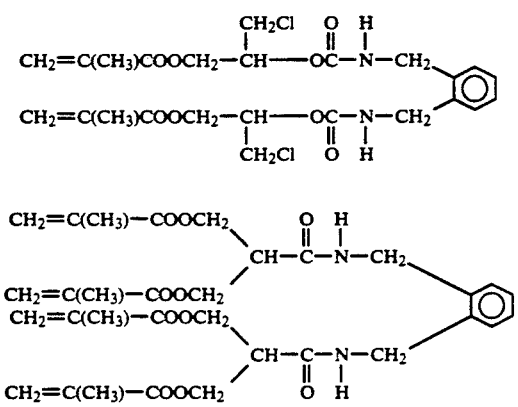

-continued

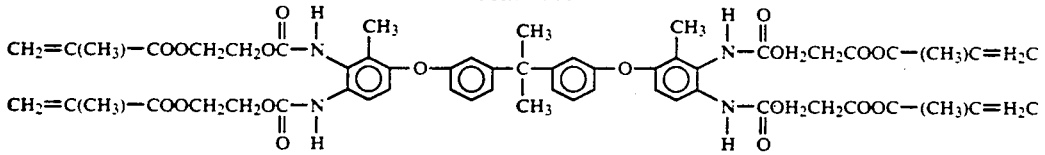

and acrylates thereof.

These may be used alone or in admixture, preferably with optional pre-addition of polymerization initiator catalysts such as an organic peroxide, e.g., benzoyl peroxide and an azo compound, e.g., azobisisobutylonitrile.

It is noted, however, that the present invention is not limited to such compounds as mentioned above.

The inorganic fillers used in the present invention may include finely divided silica powders, quartz powders, alumina powders, glass powders, kaolin, talc, calcium carbonate, barium aluminosilicate, titanium oxide, borosilicate glass, colloidal silica, colloidal alumina, atomized silica, alumina whiskers, silica whiskers, boron carbide whiskers, silicon carbide whiskers and silicon nitride whiskers, etc. and may preferably have a particle size 0.005 to 50 μm. At below 0.005 μm in particle size, the particles are so much increased in their surface area that when mixed with the polymerizable compound acting as a binder resin, they are too hard to mold. Thus, the amount of the filler incorporated throughout the enamel segment has to be inevitably decreased, resulting in no improvement in its physical properties. At longer than 50 μm in particle size, on the other hand, the enamel segment roughens on its surface, making an artificial tooth lusterless. A roughened surface is also likely to build up deposits or cause color change and coloration due to food colors, etc.

As the inorganic ingredients of the organic/inorganic composite fillers, use may be made of the same inorganic fillers as mentioned above, preferably colloidal silica, colloidal alumina or atomized silica.

As the organic/inorganic composite fillers, use may be made of all the aforesaid compounds used for the enamel and dentinal segments. These compounds may be used alone or in admixture, preferably with optional pre-addition of polymerization initiator catalysts such as an organic peroxide, e.g., benzoyl peroxide or an azo compound, e.g., azobisisobutylonitrile, and polymerized in a heating oven of 80° to 120° C., followed by pulverization in a ball mill, etc., into a particle size of 1 to 50 μm. At below 1 μm in particle size, the particles are so much increased in their surface area that when mixed with the polymerizable compound acting as a binder resin, they are too hard to mold. Thus, the amount of the filler incorporated throughout the enamel segment has to be inevitably decreased, resulting in no improvement in its physical properties. At longer than 50 μm in particle size, on the other hand, the enamel segment roughens on its surface, making an artificial tooth lusterless. A roughened surface is likely to build up deposits or cause color change and coloration due to food colors, etc.

These inorganic fillers may be used alone or in admixture, and this is true of the inorganic fillers of the organic/inorganic composite fillers. A filler comprising one or two or more of the inorganic fillers and/or one or two or more of the organic/inorganic composite fillers may suitably be used in a total quantity of 5 to 95 parts by weight with respect to 100 parts by weight of the enamel segment. If the total quantity of such fillers is less than 5 parts by weight, there is then no improvement in physical properties such as surface hardness and wear resistance. At more than 95 parts by weight, on the other hand, the absolute quantity of the polymerizable compound forming a resin matrix behaving as a resin binder is not enough to impart a given shape to the enamel segment. A filler comprising one or two or more of the inorganic fillers and/or one or two or more of the inorganic/organic composite fillers may suitably be used in a total quantity of 0.1 to 10 parts by weight with respect to 100 parts by weight of the dentinal segment. Preference is given to 0.5 to 5 parts by weight. A total quantity of such fillers less than 0.1 part by weight fails to improve the mechanical properties of the dentinal segment, whereas a total quantity of such fillers exceeding 10 parts by weight lower the adhesion between the enamel and dentinal segments. In this connection, it is noted that one or two or more of the inorganic fillers and one or two or more of the organic/inorganic composite fillers, both added to the enamel and dentinal segments, may be mixed together at any desired mixing ratio.

Preferably, the above inorganic fillers and organic/inorganic composite fillers are previously treated on their surface with a coupling agent so as to make their bonding to the matrix resin firmer. For the same purpose, they may be surface-treated by integral blending in which a coupling agent is added directly to the matrix resin.

The coupling agents used in the present invention may include organofunctional silane coupling agents, coupling agents based on titanates, coupling agents based on zircoaluminates and others. The organofunctional silane coupling agents may be γ-methacryloxypropyltrimethoxysilane, γ-glycidoxypropyltrimethoxysilane, vinyltrichlorosilane, vinyltriethoxysilane, N-β(aminoethyl)γ-aminopropyltrimethoxysilane, N-β(aminoethyl)γ-aminopropylmethyldimethoxysilane, γ-chloropropyl-trimethoxysilane and γ-aminopropyltriethoxysilane. The coupling agents based on titanates may be isopropyl triisostearoyl titanate, isopropyltridecylbenzenesulfonyl titanate, isopropyl-tris(dioctylpyrophosphate)titanate, tetraisopropyl-bis(dioctylphosphite)titanate, tetraoctyl-bis(di-tridecylphosphite)titanate tetra-(2,2-diallyloxymethyl-1-butyl)bis(ditridecyl)-phosphite titanate, bis(di-octyl pyrophosphate)oxyacetate titanate, bis(dioctyl pyrophosphate)-ethylene titanate, isopropyltrioctynol titanate, isopropyldimethacrylisostearoyl titanate, isopropyl-isostearoyldiacryl titanate, isopropyl tri(dioctyl phosphate)titanate, isopropyl tri-cumylphenyl titanate, isopropyl tri(N-aminoethyl-aminoethyl)titanate, dicumylphenyloxy acetate titanate and di-iso-stearoylethylene titanate. The coupling agents based on zircoaluminates may be alcoholic and glycolic (Cavco Mod).

Preferably, these coupling agents may be used in a quantity of 0.1 to 25 parts by weight with respect to 100 parts by weight of the above inorganic fillers and organic/inorganic composite fillers. At less than 0.1 part by weight, the coupling agents fail to fulfill their own function so that the adhesion of the inorganic fillers and organic/inorganic composite fillers to the polymerizable compound forming a matrix resin can deteriorate. Hence, the resulting artificial tooth degrades considerably in its mechanical properties. When the amount of the coupling agents added exceeds 25 parts by weight, on the other hand, the rest thereof acts as a plasticizer or a deficiency, again resulting in a drop in that mechanical properties.

Further, as the colorants used for the enamel and dentinal segments, use may be made of, e.g., red oxide, various organic pigments and oil-soluble dyes, which may be used in combination.

EXAMPLES

The present invention will now be explained specifically but not exclusively with reference to examples and comparative examples.

EXAMPLE 1

Nought decimal five (0.5) parts by weight of a polymerization initiator catalyst azobisisobutylonitrile are dissolved in 50 parts by weight of a polymerizable compound for an enamal segment, i.e., 7,7,9-trimethyl-4,13-dioxo-3,14-dioxo-5,12-diazahexa-decane-1,6-diol-dimethacrylate. A batch of this polymerizable compound is fed into a vacuum blade type of agitator, wherein it is mixed under agitation with 25 parts by weight of an inorganic filler having a mean particle size of 0.016 μm, 25 parts by weight of an organic/inorganic composite filler having a mean particle size of 25 μm, a suitable amount of a colorant red oxide adjusted to assume an enamel color and 0.5 parts by weight of a coupling agent γ-methacryloxypropyltrimethoxysilane. Then, for a dentinal segment, 65 parts by weight of polymethylmethacrylate and 25 parts by weight of methylmethacrylate are mixed under agitation with 5 parts by weight of a crosslinking agent ethylene glycol dimethacrylate, 5 parts by weight of an inorganic filler having a means particle size of 2.5 μm, 0.3 parts by weight of a polymerization initiator catalyst azobisisobutylonitrile and a suitable amount of a colorant red oxide adjusted to assume a dentinal color.

With a temperature-controllable water tank, the dentinal segment is first filled and pressed in a mold, and the product as pressed is incompletely polymerized by heating at 60° C. for 30 minutes. The product with the enamel segment laminated thereon is again filled in a mold having an extra space for the enamel segment, in which they are pressed at a pressure of about 500 kgf/cm². The product is then completely polymerized by heating at 100° C. for 15 minutes. After cooling, the product is removed from the mold to obtain a sample.

EXAMPLE 2

For an enamel segment, 50 parts by weight of a polymerizable compound having the following structural formula:

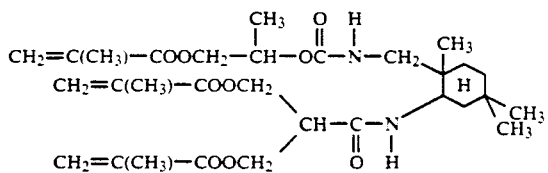

and 10 parts by weight of neopentyl glycol dimethacrylate are well-mixed together, and 0.3 parts by weight of a polymerization initiator catalyst benzoyl peroxide are dissolved in the mixture. A batch of such polymerizable compound is fed in an alumina-coated kneader, wherein they are mixed under agitation with 10 parts by weight of an inorganic filler having a mean particle size of 0.05 μm, 30 parts by weight of an inorganic/organic composite filler having a mean particle size of 25 μm, a suitable amount of a colorant red oxide adjusted to assume an enamel color and 0.4 parts by weight of a silane coupling agent γ-methacryloxypropyltrimethoxysilane for defoaming. Then, for a dentinal segment, 64 parts by weight of polymethylmethacrylate and 30 parts by weight of methylmethacrylate are mixed under agitation with 5 parts by weight of a crosslinking agent 2,2-bis(methacryloxyphenyl) propane, 1 part by weight of an organic/inorganic composite filler having a mean particle size of 25 μm, 0.18 parts by weight of a polymerization initiator catalyst benzoyl peroxide and a suitable amount of a colorant red oxide adjusted to assume a dentinal color. A sample is prepared in a similar manner as in Example 1.

EXAMPLE 3

For an enamel segment, 50 parts by weight of a polymerizable compound having the following structural formula:

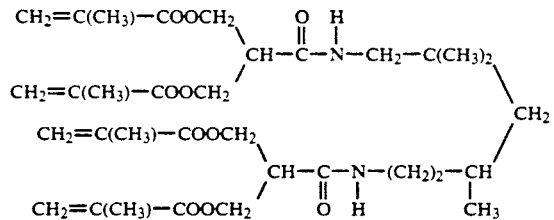

and 10 parts by weight of neopentyl glycol dimethacrylate are well-mixed together, and 0.3 parts by weight of a polymerization initiator catalyst benzoyl peroxide are dissolved in the mixture. A batch of such polymerizable compounds is fed in a mortar, wherein they are mixed under agitation with 40 parts by weight of an organic/inorganic composite filler having a means particle size of 25 μm, a suitable amount of a colorant organic pigment adjusted to assume an enamel color and 0.4 parts by weight of a silane coupling agent γ-methacryloxypropyltrimethoxysilane for defoaming. Then, for a dentinal segment, 60 parts by weight of polymethylmethacrylate and 30 parts by weight of methylmethacrylate are mixed under agitation with 5 parts by weight of a crosslinking agent 7,7,9-trimethyl-4,13-dioxo-3,14-dioxo-5,12-diazahexa-decane-1,6-diol-dimethacrylate, 1 part by weight of an inorganic filler having a mean particle size of 15 μm, 4 parts by weight of an organic/inorganic composite filler having a mean particle size of 25 μm, 0.18 parts by weight of a polymerization initiator catalyst benzoyl peroxide and a suitable amount of a colorant red oxide adjusted to assume a dentinal color. A sample is prepared in a similar manner as in Example 1.

EXAMPLE 4

For an enamel segment, 20 parts by weight of a polymerizable compound having the following structural formula:

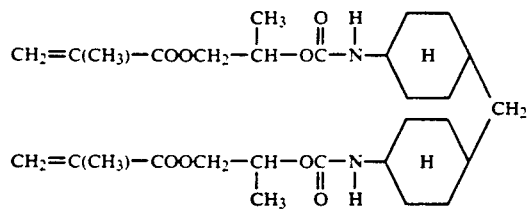

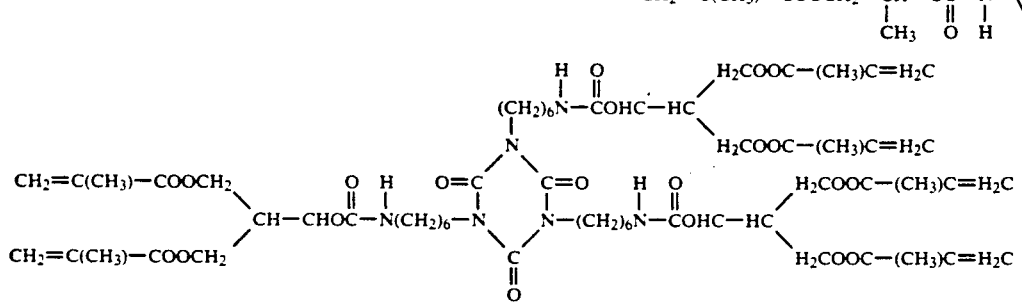

10 parts by weight of bis(methacryloxy)hydroxyethyl isocyanurate and 20 parts by weight of neopentyl glycol dimethacrylate are well-mixed together, and 0.25 parts by weight of a polymerization initiator catalyst benzoyl peroxide are dissolved in the mixture. A batch of such polymerizable compounds is fed in an alumina-coated kneader, wherein they are mixed under agitation with 25 parts by weight of an inorganic filler having a mean particle size of 2.5 μm, 25 parts by weight of an inorganic filler having a mean particle size of 15.8 μm, a suitable amount of a colorant organic pigment adjusted to assume an enamel color and 0.5 parts by weight of a γ-methacryloxypropyltrimethoxysilane for defoaming. Then, for a dentinal segment, 65 parts by weight of polymethylmethacrylate and 29 parts by weight of methylmethacrylate are mixed under agitation with 5 parts by weight of a crosslinking agent trimethylolpropane trimethacrylate, 1 part by weight of an organic/inorganic composite filler having a mean particle size of 25 μm and containing therein a colorant pre-adjusted to assume a dentinal color, 0.34 parts by weight of a polymerization initiator catalyst azobisisobutylonitrile and a suitable amount of a fine-regulating colorant oil-soluble dye adjusted to assume a dentinal color. With a hot-pressing machine, the dentinal segment is first filled and pressed in a mold, and the product as pressed is incompletely polymerized by heating at 75° C. for 15 minutes. The product with the enamel segment laminated thereon is again filled and pressed at a pressure of about 500 kgf/cm² in a mold having an extra space for the enamel segment, and the thus pressed product is completely polymerized by heating at 120° C. for 10 minutes. After cooling, the product was removed from the mold to obtain a sample.

EXAMPLE 5

For an enamel segment, 0.5 parts by weight of a polymerization initiator catalyst azobisisobutylonitrile are dissolved in 50 parts by weight of a polymerizable compound having the following structural formula:

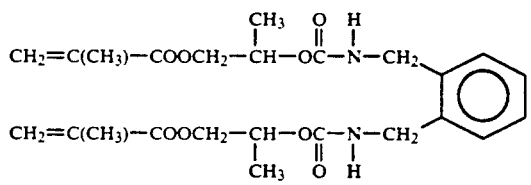

A batch of such a polymerizable compound is fed in a mortar, wherein it is mixed under agitation with 50 parts by weight of an organic/inorganic composite filler having a mean particle size of 25 μm, a suitable amount of a colorant organic pigment adjusted to assume an enamel color and 0.5 parts by weight of γ-methacryloxypropyltrimethoxysilane for defoaming. Then, for a dentinal segment, 65 parts by weight of polymethylmethacrylate and 25 parts by weight of methylmethacrylate are mixed under agitation with 5 parts by weight of a polymerizable crosslinking agent compound having the following structural formula:

$$CH_2=C(CH_3)-COOCH_2-CH(CH_3)-OC(O)-N(H)-CH_2-C_6H_{10}$$
$$CH_2=C(CH_3)-COOCH_2-CH(CH_3)-OC(O)-N(H)-CH_2-C_6H_{10}$$

1 part by weight of an organic/inorganic composite filler having a means particle size of 25 μm and containing therein a colorant preadjusted to assume a dentinal color, 4 parts by weight of an inorganic filler, 0.3 parts by weight of a polymerization initiator catalyst azobisisobutylonitrile and a suitable amount of a fine-regulating colorant that is an oil-soluble dye adjusted to assume a dentinal color. A sample is prepared in a similar manner as in Example 4.

COMPARATIVE EXAMPLE 1

Used for enamel and dentinal segments are 65 parts by weight of polymethylmethacrylate, 30 parts by weight of methylmethacrylate, 5 parts by weight of a crosslinking agent ethylene glycol dimethacrylate, 0.35 parts by weight of a polymerization initiator catalyst azobisisobutylonitrile and suitable amounts of colorants red oxide adjusted to assume enamel and dentinal colors. With a temperature-controllable water tank, the dentinal segment is first filled and pressed in a mold, and the product as pressed is incompletely polymerized by heating at 60° C. for 30 minutes. The product with the enamel segment laminated thereon is again filled and pressed at a pressure of about 500 kgf/cm² in a mold having an extra space for the enamel segment, and the product is incompletely polymerized by heating at 60° C. for 30 minutes. After the enamel and dentinal segments have been bonded together, they are completely polymerized by heating at 100° C. for 60 minutes. After cooling, the product was removed from the mold to obtain a sample.

COMPARATIVE EXAMPLE 2

Use was made of a commercially available resin tooth (the maxillary incisor) having its enamel segment hardened.

COMPARATIVE EXAMPLE 3

For an enamel segment, 40 parts by weight of 2,2-[4-(2-hydroxy-3-methacryloxyethoxyphenyl)]propane and 15 parts by weight of neopentyl glycol dimethacrylate are well-mixed together, and 0.55 parts by weight of a polymerization initiator catalyst azobisisobutylonitrile are dissolved in the mixture. A batch of such polymerizable compound is fed in a vacuum blade type of agitator, wherein they are mixed under agitation with 20 parts by weight of an inorganic filler having a mean particle size of 0.016 μm, 25 parts by weight of an organic/inorganic composite filler having a mean particle size of 25 μm, a suitable amount of a colorant red oxide adjusted to assume an enamel color and 0.45 parts by weight of γ-methacryloxypropyltrimethoxysilane. Then, for a dentinal segment, 65 parts by weight of polymethylmethacrylate and 25 parts by weight of methylmethacrylate are mixed under agitation with 5 parts by weight of a crosslinking agent ethylene glycol dimethacrylate, 5 parts by weight of an organic/inorganic composite filler having a mean particle size of 25 μm, 0.3 parts by weight of a polymerization initiator catalyst azobisisobutylonitrile and a suitable amount of a colorant red oxide adjusted to assume a dentinal color. A sample is prepared in a similar manner as in Example 4.

COMPARATIVE EXAMPLE 4

For an enamel segment, 0.4 parts by weight of a polymerization initiator catalyst are dissolved in 40 parts by weight of a polymerizable compound having the following structural formula:

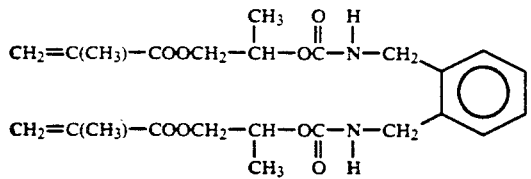

A batch of such a polymerizable compound is fed in a vacuum blade type of agitator, wherein it is mixed under agitation with 30 parts by weight of an inorganic filler having a mean particle size of 2.5 μm, 30 parts by weight of an inorganic filler having a mean particle size of 15.8 μm and a suitable amount of a colorant red oxide adjusted to assume an enamel color for defoaming. Then, for a dentinal segment, 65 parts by weight of polymethylmethacrylate and 35 parts by weight of methylmethacrylate are mixed under agitation with 0.35 parts by weight of a polymerization initiator catalyst azobisiobutylonitrile and a suitable amount of a colorant red oxide adjusted to assume a dentinal color. A sample is prepared in a similar manner as in Example 1.

COMPARATIVE EXAMPLE 5

For an enamel segment, 0.5 parts by weight of a polymerization initiator catalyst benzoyl peroxide were dissolved in 30 parts by weight of a styrene type of unsaturated polyester (available under the trade name of Polylight 8010 and made by Japan Reichhold Chemicals, Inc. A batch of this polyester is fed in a mortar, wherein it is mixed under agitation with 70 parts by weight of an inorganic filler (finely divided silica) pre-treated on its surface with 0.7 parts by weight of γ-methacryloxypropyltrimethoxysilane having a mean particle size of 15.8 μm and a suitable amount of a colorant red oxide adjusted to assume an enamel color. Then, for a dentinal segment, 65 parts by weight of polymethylmethacrylate and 35 parts by weight of methylmethacrylate are mixed under agitation with 0.35 parts by weight of a polymerization initiator catalyst azobisisobutylonitrile and a suitable amount of a colorant red oxide adjusted to assume an dentinal color. A sample is prepared in a similar manner as in Comparative Example 1.

COMPARATIVE EXAMPLE 6

In place of 7,7,9-trimethyl-4,13-dioxo-3,14-dioxo-5,12-diazahexa-decane-1,6-diol-dimethacrylate, use was made of 2,2-bis(4-methacryloxypropoxyphenyl)propane. With otherwise similar components and under otherwise similar conditions as in Example 1, a sample was prepared.

COMPARATIVE EXAMPLE 7

In place of 7,7,9-trimethyl-4,13-dioxo-3,14-dioxo-5,12-diazahexa-decane-1,6-diol-dimethacrylate, use was made of a compound having the following structural formula:

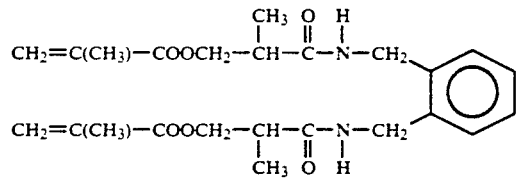

With otherwise similar components and under otherwise similar conditions as in Example 1, a sample was prepared.

PROPERTIES EVALUATED AND PROCEDURES FOR EVALUATION

1. Knoop Hardness

In a laboratory maintained constant at 23° C. +0.5° C. and a relative humidity of 50%, the labial Knoop hardness of each atificial tooth sample was measured under a load of 15 g for a loading time of 30 seconds with a Shimadzu microhardness meter, Type M, made by Shimadzu Corporation, and calculated according to the following equation:

$$H_k = \frac{14.22 \times P}{I} \times 1000$$

wherein H is the knoop hardness in kgf/mm$^2$, P is the load (kept constant at 15 g), and I is the length of a diagonal of a dent, as viewd longitudinally.

2. Deposit onto Polishing Members during Polishing

The labial side of each artificial tooth was cut to a depth of about 2 mm with a GC carborundum point No. 20. The deposition of swarf onto the point was then visually observed.

3. Labial Luster of Each Artificial Tooth Sample After the Preparation of Dentures A wax model of a denture was invested with anhydrite (GC New Plastone) in a dental flask and was cast. Each artificial tooth sample was then heated and polymerized at 70° C. for 30 minutes and 100° C. for 30 minutes) with denture base resin (GC Acron) to prepare a denture. After the denture had been taken out of the dental flask with the removal of anhydride, the labial luster of each artificial tooth sample was visually observed.

4. Coloration Testing with Food, Tobaco and Coloring Matters

Coloration tests were carried out with commercially available four items of foods, curry food (available under the trade name of Bon Curry made by Otsuka Food Industry Co., Ltd.), coffee (American Blend Coffee made by Ueshima Coffee Co., Ltd.), soy source (concentrated type of shoyu manufactured by Sanjirushi Jozo Co., Ltd.) and source (concentrated type of source manufactured by Kagome Co., Ltd.); one tobacco product, "Short Hope" (Nippon Tobacco Industry Co., Ltd.); and four coloring matters; basic fuchsine, Red No. 106 for food purposes, Blue No. 1 for medical and cosmetic purposes and Green No. 3 for medical and cosmetic purpose; nine in all. The testing conditions are set forth in Table 1, and the results of testing with the samples of the examples and comparative examples are shown in Table 2.

TABLE 1

| Curried food | Coffee | Soy source | Source | Tobacco product | Basic fuchsine | Red No. 106 | Blue No. 1 | Green No. 3 |
|---|---|---|---|---|---|---|---|---|
| During boiling 1 hour | Soy beans 100 g | During boiling 1 hour | During boiling 1 hour | Short Hope | 0.2% | 0.1% | 0.1% | 0.1% |
| | Water 300 g | | | | Aqueous solution | Aqueous solution | Aqueous solution | Aqueous solution |
| | During boiling 1 hour | | | 130 | For 20 minutes by ultra sound cleaner | During boiling 1 hour | During boiling 1 hour | During boiling 1 hour |
| Not diluted | | Not diluted | Not diluted | Water 1,000 ml | | | | |

TABLE 2

| | Example 1 | Example 2 | Example 3 | Example 4 | Example 5 | Example 6 | Example 7 | Example 8 | Example 9 |
|---|---|---|---|---|---|---|---|---|---|
| Curried food | 3 | 3 | 3 | 3 | 3 | 3 | 3 | 3 | 3 |
| Coffee | 4 | 4 | 3 | 3 | 4 | 3 | 4 | 4 | 3 |
| Soy source | 4 | 4 | 4 | 4 | 4 | 4 | 4 | 4 | 4 |
| Source | 4 | 5 | 4 | 4 | 5 | 5 | 4 | 5 | 4 |
| Tobacco product | 2 | 3 | 3 | 3 | 4 | 4 | 3 | 3 | 3 |
| Basic fuchsine | 5 | 4 | 4 | 4 | 4 | 4 | 5 | 4 | 4 |
| Red No. 106 | 4 | 4 | 5 | 4 | 4 | 4 | 5 | 4 | 4 |
| Blue No. 1 | 3 | 3 | 3 | 3 | 3 | 3 | 3 | 4 | 4 |
| Green No. 3 | 3 | 3 | 4 | 4 | 3 | 3 | 3 | 3 | 4 |
| Total | 32 | 33 | 33 | 32 | 34 | 33 | 33 | 34 | 33 |

| | Example 10 | Example 11 | Example 12 | Example 13 | Example 14 | Example 15 | Example 16 | Example 17 | Example 18 |
|---|---|---|---|---|---|---|---|---|---|
| Curried food | 3 | 3 | 3 | 3 | 3 | 3 | 3 | 3 | 4 |
| Coffee | 3 | 4 | 3 | 4 | 3 | 3 | 3 | 4 | 4 |
| Soy source | 4 | 4 | 4 | 4 | 4 | 4 | 4 | 4 | 4 |
| Source | 4 | 5 | 5 | 4 | 5 | 4 | 4 | 5 | 5 |
| Tobacco product | 3 | 3 | 4 | 3 | 4 | 3 | 3 | 4 | 3 |
| Basic fuchsine | 4 | 4 | 4 | 5 | 4 | 4 | 5 | 4 | 4 |
| Red No. 106 | 4 | 4 | 4 | 4 | 4 | 4 | 4 | 4 | 4 |
| Blue No. 1 | 3 | 3 | 3 | 3 | 4 | 4 | 3 | 4 | 3 |
| Green No. 3 | 4 | 3 | 4 | 4 | 4 | 3 | 4 | 3 | 4 |
| Total | 32 | 33 | 34 | 34 | 35 | 32 | 33 | 35 | 35 |

| | Example 19 | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|
| Curried food | 4 | 2 | 1 | 3 | 2 | 2 | 3 | 1 |
| Coffee | 4 | 4 | 1 | 3 | 1 | 1 | 4 | 1 |
| Soy source | 4 | 4 | 1 | 4 | 1 | 1 | 3 | 1 |
| Source | 4 | 4 | 3 | 4 | 2 | 2 | 4 | 2 |
| Tobacco product | 4 | 3 | 1 | 3 | 2 | 2 | 3 | 2 |
| Basic fuchsine | 5 | 3 | 2 | 3 | 2 | 2 | 3 | 2 |
| Red No. 106 | 4 | 3 | 3 | 3 | 3 | 3 | 3 | 2 |
| Blue No. 1 | 3 | 4 | 2 | 3 | 3 | 3 | 4 | 1 |
| Green No. 3 | 3 | 3 | 1 | 3 | 2 | 3 | 4 | 2 |

TABLE 2-continued

| Total | 35 | 30 | 15 | 29 | 18 | 19 | 31 | 14 |
|---|---|---|---|---|---|---|---|---|

5. Transparency of Enamel Segments

Transparency was determined in terms of total transmittance rate with a color computer SZII-Σ80 manufactured by Nippon Denshoku Industry Co., Ltd. connected to an optical system NDH for turbidimetry manufactured by the same company. For measurement, a sample was exposed at right angles to a light source of the optical system NDH for turbidimetry through an irradiation aperture of 10 mm φ according to an integral sphere method. The sample was 35 mm in diameter and 2 mm in thickness. As the present mesurement could not be carried out with an artificial tooth of actual size and, hence, a commercially available hard resin tooth was excluded.

6. Bonding of Enamel Segment to Dentinal Segment

A sample having enamel and dentinal segments, each of 2 mm in thickness, 10 mm in width and 25 mm in length was used. The dentical segment was first polymerized, and the enamel put on thereon was then formed into a final size of 4 mm in thickness, 10 mm in width and 25 mm in length. For measurement, the sample with the enamel segment up was subjected to short beam shearing testing by three-point bending at a cross head speed of 1.0 mm/min. and a span length of 20 mm with an autograph DS500 manufactured by Shimadzu Corporation. The interlaminar shear strength between the enamel and dentinal segments was obtained by the following equation:

$$\tau = \frac{3P}{4bh}$$

wherein $\tau$ is the interlaminar shear strength in kg/cm$^2$, P, the maximum load in kg, b, the width of the sample in cm and h, the thickness of the sample in cm.

In Example 1, a mixture of the compound A of the present invention (with an urethane bond cut with no phenyl group) with an organic/inorganic composite filler, a polymerization initiator catalyst and a colorant was used for the enamel segment, while a mixture of the compound B of the present invention (with neither an urethane bond nor a phenyl group) with an inorganic filler, a polymerization initiator catalyst and a colorant was employed for the dentinal segment.

In Example 2, a mixture of the compounds A and B of the present invention with an inorganic filler, an organic/inorganic composite filler, a polymerization initiator catalyst and a colorant was used for the enamel segment, while a mixture of polymethylmethacrylate, methylmethacrylate and the compound C (containing no urethane bond but having a phenyl group) with an organic/inorganic composite filler, a polymerization initiator catalyst and a colorant for the dentinal segment.

In Example 3, a mixture of the compounds, A and B of the present invention with an organic/inorganic composite filler, a polymerization initiator catalyst and a colorant was used for the enamel segment, while a mixture of polymethylmethacrylate, methylmethacrylate and the compound A with an inorganic filler, an organic/inorganic composite filler, a polymerization initiator catalyst and a colorant was employed for the dentinal segment.

In Example 4, a mixture of two compounds A and one compound B of the present invention with two inorganic fillers, a polymerization initiator catalyst and a colorant was used for the enamel segment, while a mixture of polymethylmethacrylate, methylmethacrylate and the compound B with an organic/inorganic composite filler, a polymerization initiator catalyst and a colorant was employed for the dentinal segment.

In Example 5, a mixture of the compound A of the present invention with an organic/inorganic composite filler, a polymerization initiator catalyst and a colorant was used for the enamel segment, while polymethylmethacrylate, methylmethacrylate and the compound C (with both an urethane bond and a phenyl group) with an organic/inorganic composite filler, a polymerization initiator catalyst and a colorant was employed for the dentical segment.

Essentially containing the compound A in the enamel segments, all such samples were of favorable transparency and gave more satisfactory results than did the conventional so-called hard resin teeth in the coloration tests. This is because the compound A contains an urethane bond cut includes no phenyl group. The adhesion of the enamel segments to the dentinal segments is improved and the adhesive failure is all through cohesion. This is because the compound used for the enamel segments contain no phenyl group. Additionally, the Knoop hardness of the enamel segments is superior to that of conventional resin teeth.

In Comparative Example 1, use was made of a conventional resin tooth, viz., an acrylic resin tooth made by G-C Dental Industrial Corp. This was found to have Knoop hardness of as low as 19, melted and deposited onto a carborundum point when polished with it, and took a time of as long as 120 minutes to make.

In Comparative Example 2, a commercially available hard resin tooth was used. As its dentinal segment contained neither an inorganic filler nor an organic/inorganic composite filler whatsoever, its enamel segment was not deposited onto a carborundum point when polished with it. Still, that tooth was necessarily deposited onto the polishing member upon polishing effected to the depht of its dentinal segment. In particular, the result of coloration testing was unfavorable, implying that this tooth was very likely to be colored by food colors or various pigments.

In Comparative Example 3, a mixture of the compound C (containing no urethane bond but including a phenyl group) and the compound B with an inorganic filler, an organic/inorganic composite filler, a polymerization initiator catalyst and a colorant was used for the enamel segment, while a mixture of polymethylmethacrylate, methylmethacrylate and the compound B with an organic/inorganic composite filler, a polymerization initiator catalyst and a colorant was employed for the dentical segment.

In Comparative Example 4, a mixture of the compound D (containing both an urethane bond and a phenyl group) with an inorganic filler, a polymerization initiator catalyst and a colorant was used for the enamel segment, while a mixture of polymethylmethacrylate and methylmethacryalte with a polymerization initiator catalyst and a colorant was employed for the dentinal segment.

In Comparative Example 5, an unsaturated polyester resin (the compound C with no urethane bond but with a phenyl group) was used for the enamel segment, while the same components as in Comparative Example 4 were employed for the dentical segment.

These samples pose no problem in connection with Knoop hardness and luster in the form of artificial teeth used in the preparation of a denture. However, such sample obtained with the compound containing no urethane bond cut including a phenyl group as in Comparative Examples 3 and 5 cannot be used as artificial teeth at all, since their enamel segments are very poor in transparency. Referring to such a sample obtained with the compound containing both an urethane bond and a phenyl group as in Comparative Example 4, the result of coloration testing in quite unfavorable, although its enamel segment is of favorable transparency. Eventually, this sample is so likely to be dyed with natural or synthetic colorants that from the clinical viewpoint; it cannot stand up to prolonged use in the oral cavity due to color change and coloration.

In Comparative Example 6, 2,2-bis(4-methacryloxypropoxyphenyl) propane that was the compound C containing no urethane bond but including a phenyl group of was used in place 7,7,9-trimethyl-4,13-dioxo-3,14-dioxo-5,12-diazahexa-decane-1,6-diol-dimethacrylate used in Example 1 was used a sample was prepared with otherwise similar components and under otherwise similar conditions as in Example 1. In Example 1 in which the compound A containing an urethane bond but including no phenyl group was used for the enamel segment, the transparency of the enamel segment was favorable as expressed in terms of a total transmittance of as high as 68%, but in Comparative Example 6 in which the compound C containing no urethane bond but including a phenyl group was used, the transparency of the enamel segment was quite unfavorable as expressed in terms of total transmittance of as low as 29%. This implies that a compound containing no urethane bond but including a phenyl group may not be used as the enamal segment of an artificial tooth from the aesthetic viewpoint.

In Comparative Example 7, the Compound D (containing both an urethane bond and a phenyl group) having the following structural formula:

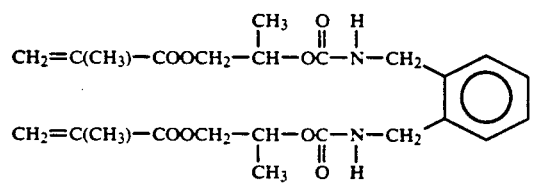

was used in place of 7,7,9-trimethyl-4,13-dioxo-3,14-dioxo-5,12-diazahexa-decane-1,6-diol-dimethacrylate and a sample was prepared with otherwise similar components and under otherwise similar conditions as in Example 1. Since both an urethane bond and a phenyl group are contained in the structural formula, the transparency of the enamel segment is favorable as expressed in terms of a total transmittance of as high as 65%, but the result of coloration testing is as low as 14, the figure implying that the sample is likely to be dyed with various colorants. In both Comparative Examples 6and 7 wherein the enamel segments were formed of a phenyl group-containing compounds, they showed quite unfavorable adhesion to the dentinal segments, event when prepared under the same conditions as in Example 1.

The results of evaluation of Examples 1–15 and Comparative Examples 1–7 are set forth in Table 3.

TABLE 3

| | Example 1 | Example 2 | Example 3 | Example 4 | Example 5 | Comparative Example 1 | Comparative Example 2 |
|---|---|---|---|---|---|---|---|
| Knoop Hardness (Enamel segment) | 45 | 42 | 45 | 44 | 45 | 19 | 29 |
| Deposites on polishing member | Not deposited | Not deposited | Not deposited | Not deposited | Not deposited | deposited | * |
| Luster on enamel segment surface after molding of dentures | Good | Good | Good | Good | Good | Poor | Good |
| Results of coloration test | 32 | 33 | 33 | 32 | 34 | 30 | 15 |
| Transparency of enamel segment (Total transparency rate %) | 68 | 65 | 65 | 69 | 71 | 69 | Unable to measure |
| Adhesion between enamel and dentinal segments (kgf/cm$^2$) | 144 | 138 | 133 | 141 | 130 | 125 | Unable to measure |
| Time in making (min.) | 45 | 45 | 45 | 25 | 25 | 120 | Unable to measure |

| | Comparative Example 3 | Comparative Example 4 | Comparative Example 5 | Comparative Example 6 | Comparative Example 7 |
|---|---|---|---|---|---|
| Knoop Hardness (Enamel segment) | 44 | 45 | 42 | 45 | 44 |
| Deposites on polishing member | Not deposited | * | * | Not deposited | Not deposited |
| Luster on enamel segment surface after molding of dentures | Good | Good | Good | Good | Good |
| Results of coloration test | 29 | 18 | 19 | 31 | 14 |
| Transparency of enamel segment (Total transparency rate %) | 31 | 65 | 22 | 29 | 65 |
| Adhesion between enamel and dentinal segments (kgf/cm$^2$) | 29 | 61 | 28 | 49 | 60 |

TABLE 3-continued

| Time in making (min.) | 25 | 120 | 120 | 45 | 45 |
|---|---|---|---|---|---|

*. Not deposited on enamel segment, deposited on dentinal segment
: Failures are all through cohesion
: Failures are of peeling on surface For a better understanding of the present invention, Examples 6-19 were performed. The components used and the results of evaluation are set forth in Table 4. Samples of Examples 6-14 were obtained in a similar manner as in Example 1, and samples of Example 15-19 were prepared in a similar manner as in Example 4. In Examples 6-8 and 17, the compound A containing an urethane bond but including no phenyl group was used as the compounds for the enamel segments. In the rest, both the compound A containing an urethane bond but including no phenyl group and the compound B containing neither an urethane bond nor a phenyl group were used as the compounds for the enamel segments.

Throughout Examples 6-19, the dentinal segments contained polymethylmethacrylate and methylmethacrylate as primary components and additionally included as the crosslinking agents for resistance to heat, solvents and weather one or two or more of the compounds consisting of one or two or more compounds A; one or two or more compounds B, one or two or more compounds C; and one or two or more compounds D. The samples are all composed of the components as shown in Table 4, and the results of evaluation indicate that they can be used as artificial teeth with no problem at all.

TABLE 4

| | | | Example 6 | Example 7 | Example 8 | Example 9 | Example 10 | Example 11 | Example 12 | Example 13 | Example 14 | Example 15 | Example 16 | Example 17 | Example 18 | Example 19 |
|---|---|---|---|---|---|---|---|---|---|---|---|---|---|---|---|---|
| Enamel segment | Note 1 | Note 2 | 60 | | | | | | | | | | | | | |
| | | Note 3 | | 60 | | | | | | | | | | | | |
| | | Note 4 | | | 60 | | | | | | | | | | | |
| | Note 6 | Note 5 | | | | 50 | 50 | 30 | 20 | 20 | 20 | 20 | 30 | 40 | 20 | |
| | | Note 7 | | 20 | | 10 | | 20 | 10 | 10 | 10 | 10 | 20 | | | |
| | | Note 8 | | | | | | | | | 35 | 35 | | | | |
| | | Note 9 | | 20 | | 40 | 40 | 10 | 20 | 20 | | | 10 | 55 | 20 | |
| | Powdery silica | | 35 | | 29 | | | 1 | 5 | 50 | 5 | 5 | 5 | 5 | 0.5 | 18 |
| | Colloidal silica | Note 10 | 5 | | 1 | | | 39 | | | 30 | | 35 | | 25.5 | 52 |
| | | Note 11 | | | 10 | | | | 45 | | | 30 | | | 34.0 | |
| | Benzoyl peroxide | | 0.30 | 0.30 | 0.30 | 0.30 | 0.30 | 0.60 | 0.50 | 0.50 | 0.65 | 0.65 | 0.60 | 0.40 | 0.20 | 0.30 |
| | Azobisisobutylonitrile | | | | | | | | | | | | | | | |
| | Red oxides | | Slight amount | Slight amount | Slight amount | Slight amount | Slight amount | Slight amount | Slight amount | Slight amount | Slight amount | Slight amount | Slight amount | Slight amount | Slight amount | Slight amount |
| | Oil-soluble dyes | | | | | | | | | | | | | | | |
| Dentinal segment | Polymethylmethacrylate | | 60 | 60 | 60 | 60 | 60 | 60 | 60 | 60 | 55 | 55 | 55 | 65 | 65 | 60 |
| | Methylmethacrylate | | 30 | 27.5 | 25 | 30 | 27.5 | 30 | 34 | 30 | 35 | 35 | 34 | 30 | 30 | 32 |
| | Note 1 | | 2.5 | 5 | | | | | | | | | | | | |
| | Note 6 | | | | 3 | 6 | 5 | 5 | | | 5 | 5 | 2 | 2 | 2 | |
| | | Note 7 | 2.5 | 3 | 3 | | | | | | | | 2 | | 1 | |
| | Note 8 | | | | | | | | | | | | | | | |
| | | Note 12 | | | | | | | | | | | 3 | | | |
| | Note 14 | | | | | | | | | | | | | | | |
| | | Note 15 | 4 | 0.5 | 1 | 2 | 6 | 2 | 5 | 4 | 4.5 | 4.5 | 1 | 0.5 | | 7.5 |
| | Note 16 | | | | | | | | | | | | | | | |
| | | Note 17 | 1 | 1 | 0.5 | 2 | | 2 | | 4 | | | 1 | | | |
| | Powdery silica | | | | | | | 0.5 | 0.5 | 0.5 | 0.3 | 0.2 | 0.5 | 0.1 | 0.5 | 0.5 |
| | Colloidal silica | Note 10 | | 0.5 | 0.5 | | 0.5 | 0.5 | 0.5 | 0.5 | 0.2 | 0.1 | | 0.1 | 0.05 | |
| | | Note 11 | | | | | 1 | | | 0.5 | | 0.1 | 0.5 | 0.4 | 0.45 | |
| | | | | | | | | | | | | 0.1 | | | 0.5 | |
| | Benzoyl peroxide | | 0.18 | 0.20 | 0.19 | 0.18 | 0.20 | 0.39 | 0.39 | 0.38 | 0.45 | 0.45 | 0.44 | 0.18 | 0.34 | 0.40 |
| | Azobisisobutylonitrile | | | | | | | | | | | | | | | |
| | Red oxides | | Slight amount | Slight amount | Slight amount | Slight amount | Slight amount | Slight amount | Slight amount | Slight amount | Slight amount | Slight amount | Slight amount | Slight amount | Slight amount | Slight amount |
| | Oil-soluble dyes | | | | | | | | | | | | | | | |
| Item of evaluation | Knoop hardness(enamel segment) | | 41 | 41 | 40 | 41 | 40 | 39 | 44 | 43 | 40 | 39 | 39 | 45 | 44 | 48 |
| | Deposits on polishing member | | Not deposited | Not deposited | Not deposited | Not deposited | Not deposited | Not deposited | Not deposited | Not deposited | Not deposited | Not deposited | Not deposited | Not deposited | Not deposited | Not deposited |
| | Luster on enamel segment surface after molding of dentures | | Good | Good | Good | Good | Good | Good | Good | Good | Good | Good | Good | Good | Good | Good |
| | Results of coloration test (Table 3) | | 33 | 33 | 34 | 33 | 32 | 33 | 34 | 34 | 35 | 32 | 33 | 35 | 35 | 35 |
| | Transparency of enamel segment (Total transparency rate %) | | 66 | 62 | 67 | 68 | 69 | 65 | 70 | 66 | 64 | 69 | 72 | 68 | 68 | 70 |
| | Adhesion between enamel and dentinal segments (kgf/cm$^2$) | | 145* | 138* | 133* | 125* | 135* | 132* | 141* | 142* | 150* | 135* | 137* | 144* | 142* | 147* |
| | Time in making (min.) | | 45 | 45 | 45 | 45 | 45 | 45 | 45 | 45 | 45 | 25 | 25 | 25 | 25 | 25 |

TABLE 4-continued

*Failures are all through cohesion
All units of the figures in the Table for enamel and dentinal segments are in part by weight. One part by weight of γ-methacryloxypropyltrimethoxysilane per 100 parts by weight of inorganic fillers and organic/inorganic composite fillers has been added to respective polymerizable compounds.
Note 1 Polymerizable compound with an urethane bond but with no phenyl group and containing at least two ethylenically unsaturated double bond.
Note 2 7,7,9-trimethyl-4,13-dioxo-5,12-diazahexa-decane-1,6-diol-dimethacrylate.

Note 3
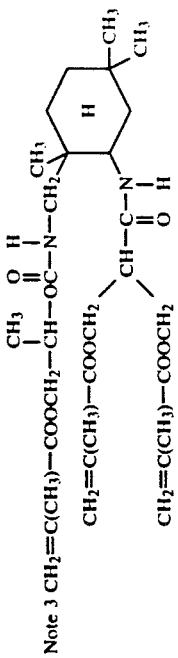

Note 4
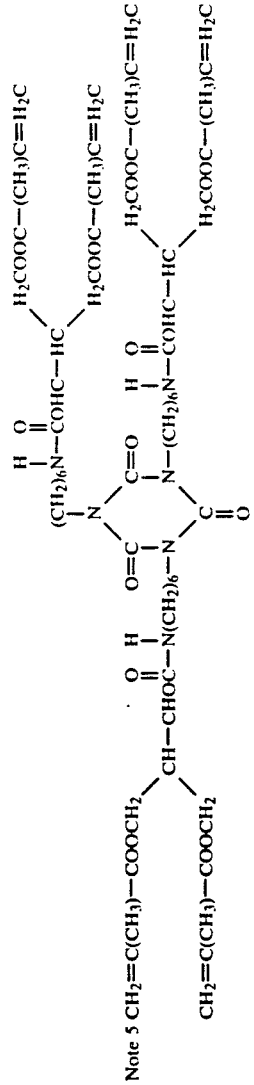

Note 5 similar structure

Note 6 Polymerizable compound with neither a urethane bond nor a phenyl group and containing at least two ethylenically unsaturated double bonds.
Note 7 Ethylene glycol dimethacrylate.
Note 8 Neopentyl glycol dimethacrylate.
Note 9 Trimethylolpropane trimethacrylate.
Note 10 Organic/inorganic composite filler (with the organic component being trimethylolpropane trimethacrylate and the inorganic component being colloidal silica).
Note 11 Organic/inorganic composite filler (with the organic component being 7,7,9-trimethyl-4,13-dioxo-3,14-diazahexa-decane-1,6-diol-dimethacrylate and the inorganic component being colloidal silica).
Note 12 Polymerizable compound with no urethane bond but with a phenyl group and containing at least two ethylenically unsaturated double bonds.
Note 13 2,2-bis(4-methacryloxypropoxyphenyl)propane.
Note 14 2,2-bis [4-(2-hydroxy-3-methacryloxyethoxyphenyl)]propane.
Note 15 Polymerizable compound with both a urethane bond and a phenyl group and containing at least two ethylenically unsaturated double bonds.

TABLE 4-continued
Note 16 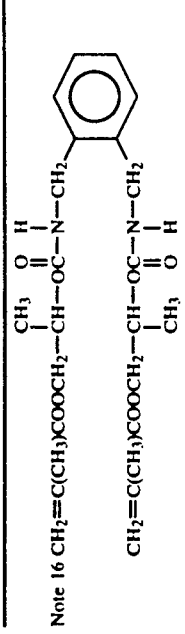
Note 17 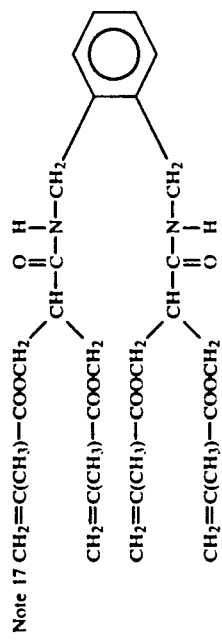

EFFECT OF THE INVENTION

The artificial tooth according to the present invention comprises an enamel segment in which a resin matrix is primarily composed of one or two or more compounds A containing an urethane bond but including no phenyl group with or without one or two or more compounds B containing neither an urethane bond nor a phenyl group and formed into a composite material with a filler; and a dentinal segment formed of a material in which a filler is optionally added to a component obtained by crosslinking polymethylmethacrylate and methylmethacrylate with one or two or more of the compounds consisting of one or two or more compounds A; one or two or more of the compounds B; one or two or more of the compounds C containing no urethane bond but including a phenyl group; and one or two or more compounds D containing both an urethane bond and a phenyl group. The method for making an artificial tooth according to the present invention involves first incomplete polymerization of the dentinal segment and, just after the enamel segment being put thereon, final complete polymerization of both the segments. This method makes a breakthrough in the art and so produces the following effects.

(1) The enamel segment of the artificial tooth according to the present invention has a surface Knoop hardness of 40-45, the figure being bigger by about 2-3 times than that of a conventional resin tooth. Thus, the enamel segment is very unlikely to wear away, suffer damage or deform due to attrition or strong chewing at the time of mastication and repeated contact with a toothbrush.

(2) The enamel and dentinal segments according to the present invention are formed of a composite material with a filler comprising one or two or more of the inorganic fillers and/or one or two or more of the organic/inorganic composite fillers. Hence, dental operations using a carborundum point or a stamp bar with a dental engine are very expedited when milling-in is carried out for the purpose of occlusal equilibration, since it is unlikely that the artificial tooth according to the present invention may be deposited onto such polishing members with the resulting drop in polishing efficiency.

(3) Where a denture is prepared with the use of the artificial tooth according to the present invention, it is by no means likely that the artificial tooth may be brought into firm contact with gypsum so that the rough surface of gypsum may be impressed thereon, making the surface thereof lusterless, since it is lower in its coefficient of thermal expansion and higher in its surface hardness than a conventional resin tooth.

(4) The artificial tooth according to the present invention is much more unlikely to suffer color change and coloration in the oral cavity due to deposits or natural or synthetic food colors, as compared with the conventional so-called hard resin tooth making use of the compound D containing both an urethane bond and a phenyl group.

(5) The enamel segment of the artificial tooth according to the present invention suffers little or no drop in transparency, even when it is formed into a composite material with a filler comprising one or two or more of the inorganic fillers and/or one or two or more of the organic/inorganic composite filler. Satisfactory transparency makes it possible to give every color tone to an artificial tooth and to impart a deep color tone to the enamel segment. Even upon wetted with saliva or water, the present artificial tooth is not clouded at all, unlike the conventional so-called hard resin tooth, thus posing no aesthetic problem even when used for clinical purposes.

(6) The artificial tooth according to the present invention shows much improved enamel-to-dentine adhesion, since used for the enamel segment is the compound A containing an urethane bond but including no phenyl group with or without the compound B containing neither an urethane bond nor a phenyl group. Hence, it is unlikely that the enamel segment may be peeled off from the dentinal segment, even when a filler is added to the latter. Therefore, the dentinal segment is improved in terms of mechanical properties such as wear resistance.

(7) The artificial tooth according to the present invention shows much improved enamel-to-dentine adhesion. Thus, if only the dentinal segment is first incompletely polymerized at a temperature of 60°-70° C. for about 15-30 minutes, the enamel and dentinal segments can then be bonded together with no generation of air bubbles in the enamel segment. Later, overlapping portions of both segments can be completely polymerized simultaneously at 90°-120° C. for about 10-30 minutes. This method takes 25-60 minutes for one cycle of the operation to be completed, the figure being about one-third or fourth of the length of a conventional cycle.

What is claimed is:

1. An artificial tooth comprised of enamel and dentinal segments, said enamel segment comprising: (i) one or two or more polymerizable compounds with an urethane bond but with no phenyl group and containing at least two ethylenically unsaturated double bonds; or a compound consisting of one or two or more polymerizable compounds with an urethane bond but with no phenyl group and containing at least two ethylenically unsaturated double bonds and one or two or more polymerizable compounds with neither urethane bond nor phenyl group and containing at least two ethylenically unsaturated double bonds; (ii) a filler consisting of one or two or more inorganic fillers and/or one or two or more organic/inorganic composite fillers; (iii) a polymerization initiator catalyst; and (iv) a colorant.

2. An artificial tooth comprised of enamel and dentinal segments, said dentinal segment comprising: (i) polymethylmethacrylate; (ii) methylmethacrylate; (iii) a compound consisting of the following four compounds (a)-(b) alone or in combination, (a) one or two or more polymerizable compounds A with an urethane bond but with no phenyl group and containing at least two ethylenically unsaturated double bonds, (b) one or two or more polymerizable compounds B with neither an urethane bond nor a phenyl group and containing at least two ethylenically unsaturated double bonds, (c) one or two or more polymerizable compounds C with no urethane bond but with a phenyl group and containing at least two ethylenically unsaturated double bonds, and (d) one or two or more polymerizable compounds D with both an urethane bond and a phenyl group and containing at least two ethylenically unsaturated double bonds; (iv) a filler consisting of one or two or more inorganic fillers and/or one or two or more organic/inorganic composite fillers; (v) a polymerization initiator catalyst; and (vi) a colorant.

3. An artificial tooth comprised of enamel and dentinal segments, (I) said enamel segment comprising: (i) one or two or more polymerizable compounds with an urethane bond but with no phenyl group and containing at least two ethylenically unsaturated double bonds; or a compound consisting of one or two or more polymerizable compounds with an urethane bond but with no phenyl group and containing at least two ethylenically unsaturated double bonds and one or two or more polymerizable compounds with neither urethane bond nor phenyl group and containing at least two ethylenically unsaturated double bonds; (ii) a filler consisting of one or two or more inorganic fillers and/or one or two or more organic/inorganic composite fillers; (iii) a polymerization initiator catalyst; and (iv) a colorant, and (II) said dentinal segment comprising: (i) polymethylmethacrylate; (ii) methylmethacrylate; (iii) a compound consisting of the following four compounds (a)-(b) alone or in combination, (a) one or two or more polymerizable compounds A with an urethane bond but with no phenyl group and containing at least two ethylenically unsaturated double bonds, (b) one or two or more polymerizable compounds B with neither an urethane bond nor a phenyl group and containing at least two ethylenically unsaturated double bonds, (c) one or two or more polymerizable compounds C with no urethane bond but with a phenyl group and containing at least two ethylenically unsaturated double bonds, and (d) one or two or more polymerizable compounds D with both an urethane bond and a phenyl group and containing at least two ethylenically unsaturated double bonds; (iv) a filler consisting of one or two or more inorganic fillers and/or one or two or more organic/inorganic composite fillers; (v) a polymerization initiator catalyst; and (vi) a colorant.

4. A method for making an artificial tooth comprised of enamel and dentinal segments, (I) said enamel segment comprising: (i) one or two or more polymerizable compounds with an urethane bond but with no phenyl group and containing at least two ethylenically unsaturated double bonds; or a compound consisting of one or two or more polymerizable compounds with an urethane bond but with no phenyl group and containing at least two ethylenically unsaturated double bonds and one or two or more polymerizable compounds with neither an urethane bond nor a phenyl group and containing at least two ethylenically unsaturated double bonds; (ii) a filler consisting of one or two or more inorganic fillers and/or one or two or more organic/inorganic composite fillers; (iii) a polymerization initiator catalyst; and (iv) a colorant, and (II) said dentinal segment comprising: (i) polymethylmethacrylate; (ii) methylmethacrylate; (iii) a compound consisting of the following four compounds (a)-(b) alone or in combination, (a) one or two or more polymerizable compounds A with an urethane bond but with no phenyl group and containing at least two ethylenically unsaturated double bonds, (b) one or two or more polymerizable compounds B with neither two ethylenically unsaturated double bonds, (c) one or two or more polymerizable compounds C with no urethane bond but with a phenyl group and containing at least two ethylenically unsaturated double bonds, and (d) one or two or more polymerizable compounds D with both an urethane bond and a phenyl group and containing at least two ethylenically unsaturated double bonds; (iv) a filler consisting of one or two or more inorganic fillers and/or one or two or more organic/inorganic composite fillers; (v) a polymerization initiator catalyst; and (vi) a colorant; wherein: said dentinal segment is first incompletely polymerized without incomplete polymerization of said enamel segment, and said enamel segment is then completely polymerized simultaneously with complete polymerization of said dentinal segment.

* * * * *